US012753434B2

(12) United States Patent
Lundquist et al.

(10) Patent No.: US 12,753,434 B2
(45) Date of Patent: Oct. 6, 2026

(54) SEQUENCING SYSTEMS AND METHODS UTILIZING CURVED IMAGING PATHS ON ROTATING SUBSTRATES

(71) Applicant: MGI Tech Co., Ltd., Shenzhen (CN)

(72) Inventors: Paul Lundquist, Oakland, CA (US); Chintang Yen, San Jose, CA (US); Andriy Tspuryk, San Jose, CA (US); Joon Yang, Redwood City, CA (US); Jon Bartman, Mountain View, CA (US); Razvan Chirita, Redwood City, CA (US); Jay Shafto, Mountain View, CA (US); Michelle Jarrell, Gilroy, CA (US); Wei Wang, San Jose, CA (US); Clark Reyes, San Jose, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 1055 days.

(21) Appl. No.: 17/839,829

(22) Filed: Jun. 14, 2022

(65) Prior Publication Data

US 2022/0403466 A1 Dec. 22, 2022

Related U.S. Application Data

(60) Provisional application No. 63/211,775, filed on Jun. 17, 2021.

(51) Int. Cl.
*C12Q 1/6874* (2018.01)
*B01L 3/00* (2006.01)
*G01N 21/64* (2006.01)

(52) U.S. Cl.
CPC ...... *C12Q 1/6874* (2013.01); *B01L 3/502715* (2013.01); *B01L 3/502761* (2013.01); *G01N 21/6428* (2013.01); *G01N 21/6456* (2013.01); *B01L 2200/16* (2013.01); *B01L 2300/0654* (2013.01); *B01L 2300/0803* (2013.01); *G01N 2021/6439* (2013.01)

(58) Field of Classification Search
CPC ............. C12Q 1/6874; B01L 3/502715; B01L 3/502761; B01L 3/50273; B01L 2200/16; B01L 2300/0654; B01L 2300/0803; B01L 2400/0409; G01N 21/6428; G01N 21/6456; G01N 21/6452; G01N 2021/6439; G01N 2201/0415; G01N 2201/1045
See application file for complete search history.

(56) References Cited

U.S. PATENT DOCUMENTS

| | | | |
|---|---|---|---|
| 10,273,528 | B1 | 4/2019 | Barbee et al. |
| 10,351,846 | B2 | 7/2019 | Boutell et al. |

FOREIGN PATENT DOCUMENTS

| | | | | |
|---|---|---|---|---|
| CN | 1677075 | | 10/2005 | |
| CN | 104379762 | | 2/2015 | |
| CN | 205528708 | | 8/2016 | |
| CN | 207468611 | | 6/2018 | |
| CN | 208857264 | | 5/2019 | |
| CN | 208857264 U | * | 5/2019 | |
| WO | 2020186243 | | 9/2020 | |
| WO | WO-2020186243 A1 | * | 9/2020 | .............. B01J 4/007 |

OTHER PUBLICATIONS

International Application No. PCT/CN2022/099342, International Preliminary Report on Patentability mailed on Dec. 28, 2023, 8 pages.
International Application No. PCT/CN2022/099342, International Search Report and Written Opinion mailed on Sep. 14, 2022, 12 pages.

* cited by examiner

*Primary Examiner* — Robert T. Crow
*Assistant Examiner* — Allison E Schloop
(74) *Attorney, Agent, or Firm* — Kilpatrick Townsend & Stockton LLP

(57) ABSTRACT

A nucleic acid sequencing system may include a substrate coupled to a rotating disk. The substrate may include a plurality of nucleic acid samples. A detection system, including for example an objective and a camera, may detect sequencing events on the substrate while the substrate is rotated relative to the detection system around a rotational axis of the substrate, perpendicular to a surface of the substrate, by the actuation system.

20 Claims, 16 Drawing Sheets

SEQUENCING SYSTEMS AND METHODS UTILIZING CURVED IMAGING PATHS ON ROTATING SUBSTRATES

CROSS REFERENCE TO RELATED APPLICATIONS

This patent application relates to and claims priority to U.S. provisional patent application Ser. No. 63/211,775 filed Jun. 17, 2021, the entire contents of which are hereby incorporated by this reference.

RELATED FIELDS

This disclosure relates to systems for nucleic acid sequencing and other biochemical analyses.

BACKGROUND

Nucleic acid sequencing includes numerous different costs, for example, costs related to the purchase and upkeep of the sequencing device. Reducing the amount of time to produce the same amount of sequencing data compared to existing sequencing devices may reduce the overall costs of producing the sequencing data.

Some currently available sequencing systems detect sequencing events on an essentially rectangular 2-dimensional planar substrate of a flowcell. An objective of an optical detection system and the flowcell are moved along straight paths relative to each other so that the field of view of the objective is passed over the substrate a plurality of times along parallel paths, wherein each pass images a portion of the substrate so that the entire substrate is imaged. These systems have the disadvantages of needing to slow, stop, and/or change the direction of the relative movement of the objective of the optical system relative to the substrate between the multiple straight path transits over a flowcell needed to image the entire substrate of the flowcell. This leads to periods of time during the overall imaging process during which imaging of the substrate is not taking place due to the need to position and control the relative movement of the system components in order to resume imaging. Accordingly, there is a need to reduce or eliminate this downtime.

BRIEF SUMMARY

This present technology relates to systems and methods for detecting sequencing events. The systems and methods may be employed in, for example, sequencing nucleic acid molecules disposed on a substrate, wherein the substrate may include from millions to billions of individual nucleic acid sites. The substrate may be formed or coupled to a rotatable disk. The disk may rotate and translate relative to a field of view (FOV) of a detection system, for example an objective of an optical detection system, so that the FOV passes over the substrate in curved paths (e.g. concentric circles and/or spiral paths) in order to image the sequencing events on the entire substrate. One advantage of the disclosed systems and methods for detecting sequencing events may be improved throughput due to increasing the distance of the substrate that the FOV of the imaging system can cover while continuously imaging the sequencing events on the substrate without slowing or stopping relative movement between the FOV and the substrate, thereby creating significant cost savings as will be discussed herein.

Figure 1A:
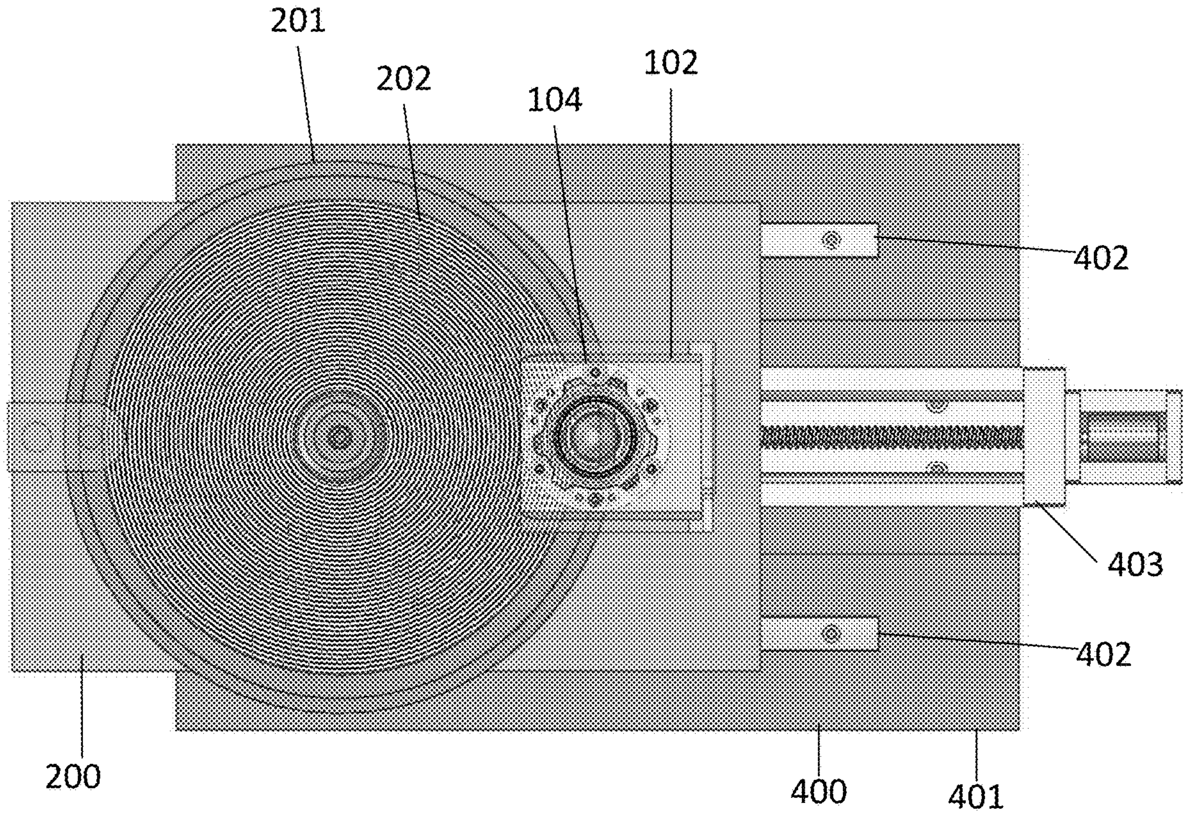
FIGS. 1A-1C show embodiments of an optical imaging system.

In accordance with common practice, the described features and elements are not drawn to scale but are drawn to emphasize features and elements relevant to the present disclosure.

DETAILED DESCRIPTION

The present disclosure describes a sequencing detection system that may be employed in detecting sequencing events on a rotating substrate. For example, the disclosed sequencing detection system may be an optical imaging system employed in sequencing for example, nucleic acids. In embodiments, the template nucleic acid molecules may be bound to, or otherwise disposed on, a surface of the substrate and then imaged by the optical imaging system.

There are many approaches to nucleic acid (e.g., DNA) sequencing. See, e.g., Kumar, K., 2019, "Next-Generation Sequencing and Emerging Technologies," *Semin Thromb Hemost* 45(07): 661-673. The most popular methods use arrays with a large number of discrete sites (e.g., 100 million to 1 billion or more) in an ordered array on a planar substrate. Typically the sites are small (e.g., characterized by a diameter or diagonal less than 1 micrometer, often less than 500 nanometers, and often in the range of 50 nanometers to 500 nanometers) and present at a high density (e.g., of more than ~~$10^6$ sites per $cm^2$). Nucleic acid templates are immobilized directly or indirectly at the individual sites for sequencing. Generally each site contains a clonal population of template sequences, such as a DNA nanoball (Complete Genomics, Inc.) or PCR products or amplicons (Illumina, Inc.). For illustration and not limitation, in these approaches nucleic acid sequences are determined one base at a time over a series of sequencing "cycles." Each cycle comprises (i) introducing reagents to each site on the array of immobilized template molecules; (ii) carrying out a series of biochemical or enzymatic reactions ("sequencing reactions") simultaneously at the sites; (iii) detecting signals at each site (zero, one or more than one signal per site per cycle) which may be referred to as "image acquisition:"; and (iv) carrying out enzymatic, washing, or regeneration steps at each site on the array so that another sequencing cycle can be carried out. Without limitation the "signals" collected in (iii) may be optical signals, e.g., fluorescence or luminescence signals. The sequencing array is usually contained in a "flow cell" through which primers, reagents, washes, etc. can be flowed. Typically a sequencing run consists of ~400 cycles, which means that ~400 or more imaging events, each involving acquiring signal individually from each of millions of sites is required. The speed and precision of image collection affects cost, efficiency, and sequencing data quality.

As used herein a "sequencing event" refers to emission of an optical signal (e.g., a fluorescence or luminescence signal) resulting from a sequencing process. An exemplary sequencing process is a cycle of a sequencing-by-synthesis process. In this approach, nucleotides are incorporated into a primer extension product (e.g. using reversible terminator nucleotides). In this approach, nucleotides can be labeled with, for example, a fluorescent dye or a source of a luminescence signal (e.g. luciferase or luciferase substrate). A luminescent signal includes chemiluminescence and bioluminescence. A nucleotide can be labeled directly with a fluorescent dye or a source of a luminescence signal or can be associated with an antibody, aptamer or other agent labeled with a signal generating moiety. In the process of sequencing a defined optical signal is produced at each site in an array by, for example, illumination of the fluorescent dye(s) with an excitation wavelength, and the signals and corresponding positions are recorded.

Although framed in the context of nucleic acid sequencing, it will be recognized that the devices and methods disclosed herein are not limited to nucleic acid sequencing uses. The system may be used, for example, for nucleic acid analysis other than sequencing (e.g., SNP analysis, real time PCR analysis) or for analysis of chemical or biochemical processes using substrates or analytes other than nucleic acids. In one aspect, the technology provides an assay system comprising a substrate coupled to a disk and defining an outer surface, wherein the disk is rotatable around a rotational axis perpendicular to the disk with an actuation system, and wherein the outer surface of the substrate is configured to support a plurality of chemical or biochemical reactions, detectable by a detection system configured to detect optical signals produced by the chemical or biochemical reactions on the substrate while substrate is rotated relative to the detection system around the rotational axis by the actuation system.

FIG. 1A shows an example of a sequencing detection system according to the present technology. As shown in the top view in FIG. 1A, a sequencing detection system comprises a detection system 102, in the form of an optical detection system including an objective 104, a disk assembly 200, and a track assembly 400. The disk assembly 200 comprises a disk 201 and a substrate 202.

The detection system 102 may be an optical detection system further including camera(s), processor(s), lens(es), illumination source(s), filter(s), mirror(s), and actuator(s) used for detecting sequencing events on the substrate 202. Examples of detection systems include one or more of objective lens, laser illumination systems, autofocus systems, systems of dichroic filters to combine illumination and detection paths and to provide paths for autofocus, and high sensitivity cameras. Cameras may, be for example, in area scan or Time-Domain-Integration (TDI) formats. For example, the detection system 102 may include a Time Delay Integration (TDI) camera with a sensor specified for 8900×256 pixels at a 500 kHz line rate.

The track assembly 400 may comprise a base 401, one or more tracks 402, for example two tracks as shown in FIG. 1A, and a linear actuator 403. The disk assembly 200 is slidably coupled to the tracks 402 in order for the linear actuator 403 to cause translation of the disk assembly 200 in one direction while restraining motion in other directions relative to the objective 204. As used herein, translation in the direction of the tracks 402 will be referred to as translation in the X-direction, in an XYZ reference frame. As will be discussed in greater detail below, translation of the disk 201 along a longitudinal axis in the X-direction, perpendicular to the rotational axis of the disk, and rotation of the disk around the rotational axis, Z-axis, is used to cause relative movement between the objective 104 and the substrate 202 in order to image sequencing events around a circumference the substrate 202.

Figure 1B:
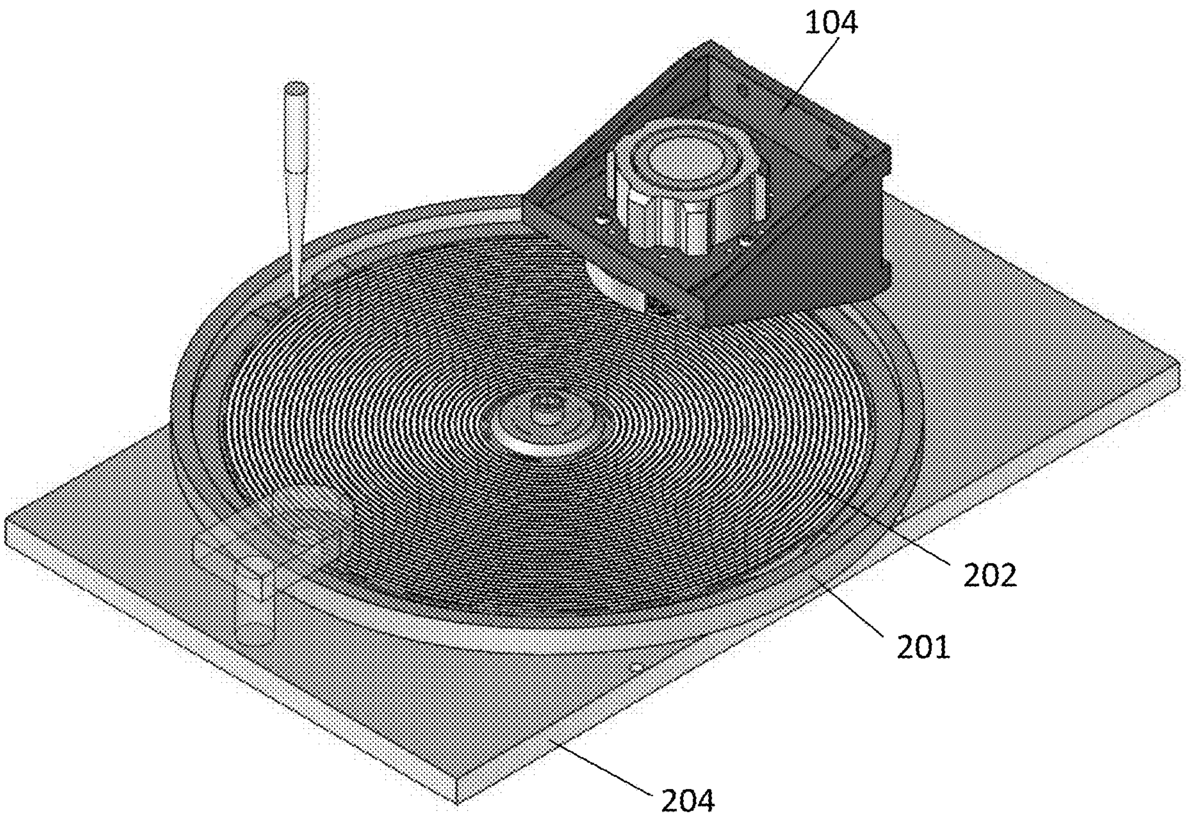

FIG. 1B, shows a portion of the sequencing detection system including the disk assembly 200 and the objective 104. The disk 201 may be generally circular and comprises one or more substrates 202 coupled to the disk. The substrate 202 may be formed of one or more sections and defines a circular substrate surface around a rotational axis of the disk 201. The disk assembly 200 further comprises a rotational actuator 203, for example a motor, as part of an actuation system of the sequencing detection system. The rotational actuator 203 is used for rotating the disk 201, and therefore the substrate 202 coupled thereto, relative to the objective 104 in order to image different portions of the substrate 202. Further, the actuation system of the sequencing detection system may include additional actuators configured to cause relative motion between the objective and the substrate in multiple degrees of freedom, for example any combination of translations in up to three orthogonal directions and/or rotations around up to three orthogonal axes.

Figure 1C:
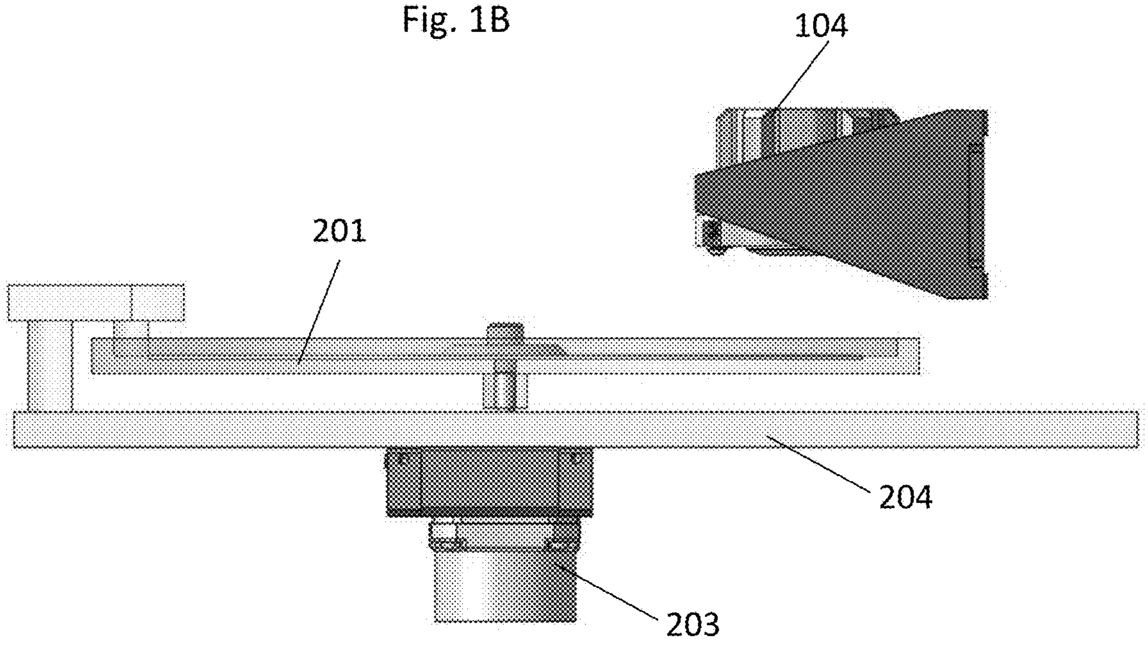

The disk assembly 200 in addition to the disk 201, includes a carriage 204 rotationally coupled to and positioned under the disk 201, as shown in FIG. 1C. As shown in FIG. 1A, the carriage is slidably coupled to the track system 400. As shown in FIG. 1B, the carriage 204 may be substantially rectangular in shape. The rotational actuator 203 may include a portion fixedly coupled to the carriage 204, and a rotatable drive shaft fixed coupled to the disk in order to rotate the disk, and substrate, relative to the carriage.

The disk 201 may comprise an axle coupled to the rotational actuator 203. The axle of the disk may extend through the carriage 204 and couple to the rotational actuator on a side of the carriage opposite the substrate. The carriage may include bearings supporting the axle of the disk and/or the drive shaft of the rotational actuator so that the disk may rotate relative to the carriage, and so that the disk 201 is restrained relative to the carriage in all but a single rotational degree of freedom. The rotational actuator 203 of the disk assembly 200 may be coupled to the axle and may be for example a stepper motor, a servo motor, or the like, in order to cause rotation of the disk 201 relative to the carriage and the objective 104 of the detection system.

The actuator 203 may include a feedback loop and/or a flywheel in order to maintain a constant rotational speed. The disk may be rotated for example between 5 RPM and 1000 RPM during imaging of the substrate. The rotational speed of the disk may be selected based on a camera frame rate and a magnification of the optical system in combination with the diameter of the disk. TDI cameras may have a frame rates between 50,000 lines/sec and 1,000,000 lines/sec. For example, a camera may have a line rate of 250,000 lines/sec and a magnification of 18×, results in a linear speed up to 72 mm/sec. The rotational speed of the disk may then be selected so that the linear speed of the surface of the substrate on the disk moving past the FOV of the camera does not exceed the linear speed of the camera system. For example, a disk with an outer diameter, i.e. the highest linear velocity portions of the disk rotated at a constant rate, of 100 mm may be selected to have a rotational speed of less than 0.23 rotations per second ((72 mm/sec)/(100 mm*pi/1 rev)

Figure 2A:
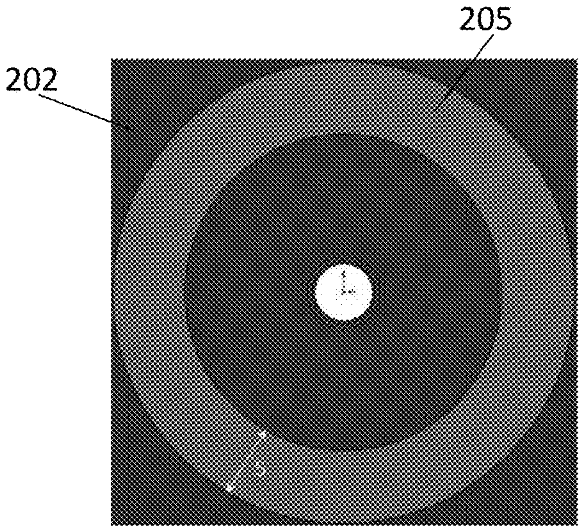
FIGS. 2A-2J show embodiments of substrate and disk assemblies and substrate assemblies.
Figure 2B:
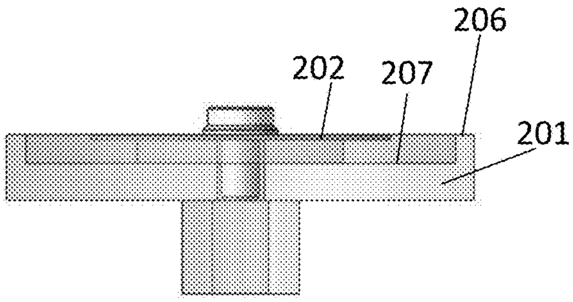
Figure 2C:
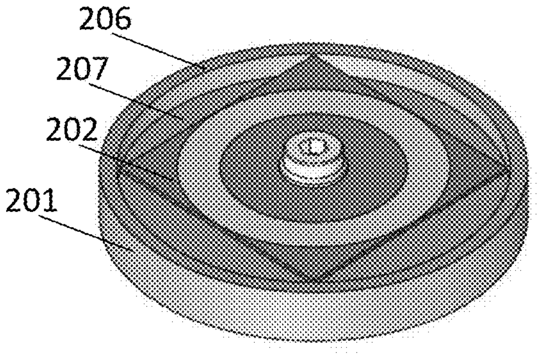
Figure 2D:
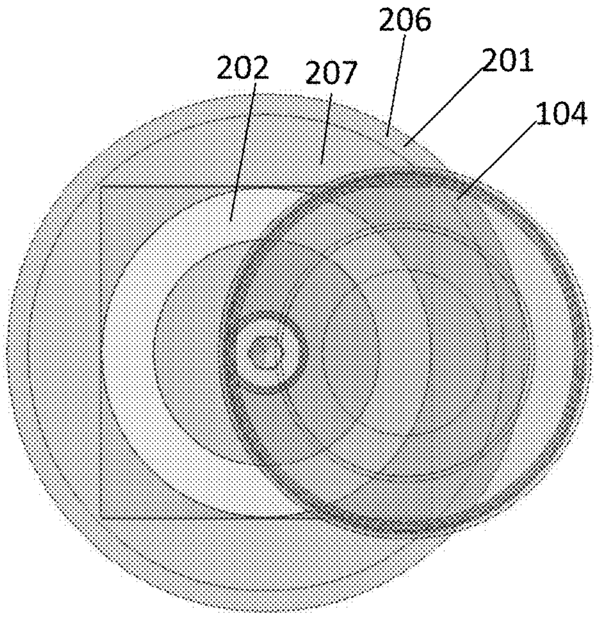

FIGS. 2A-2D show examples of a disk 201 and a substrate 202, as well as an objective 104 in some views. In embodiments, for example as shown in FIG. 2A, the substrate 202 may be square and include a circular imaging portion 205. As shown in FIGS. 2A and 2C, the disk 201 includes a perimeter wall 206 and a recessed surface 207. In embodiments, one or more substrates 202 may be integrally formed with, coupled to, or positioned above the recessed surface 207. The substrate 202 may be formed for example of silicon or $SiO_2$. The substrate may be produced from a wafer, for example a silicon wafer or a $SiO_2$ wafer. As shown in FIG. 2D, an objective may be positioned over the assembly of the disk 201 and substrate 202 to image the imaging portion 205.

Figure 2E:
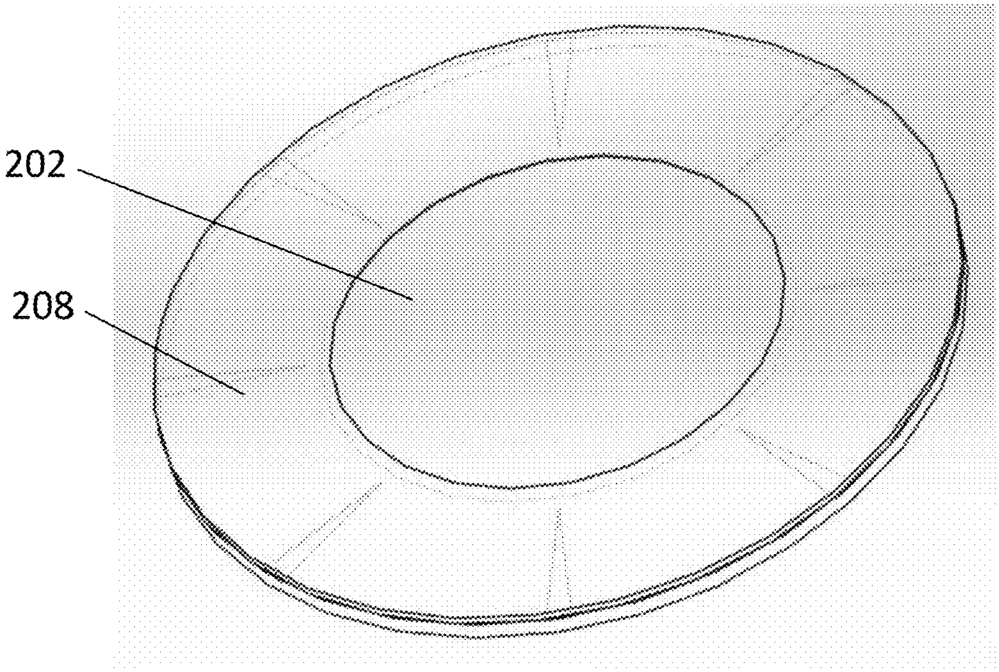
Figure 2F:
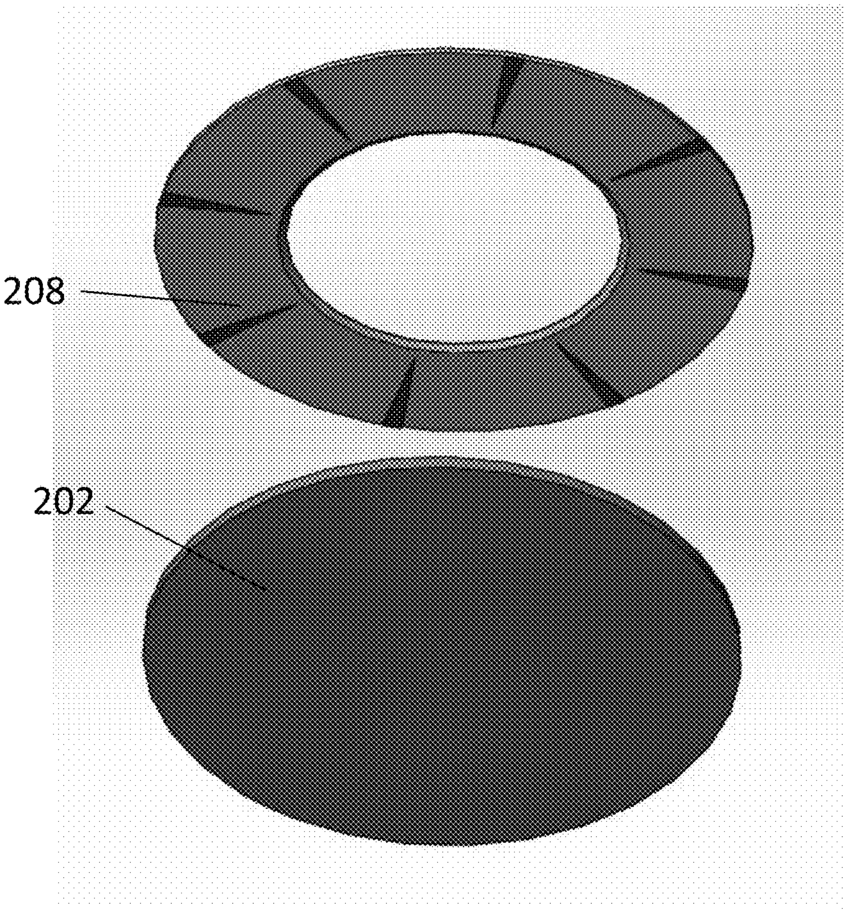
Figure 2G:
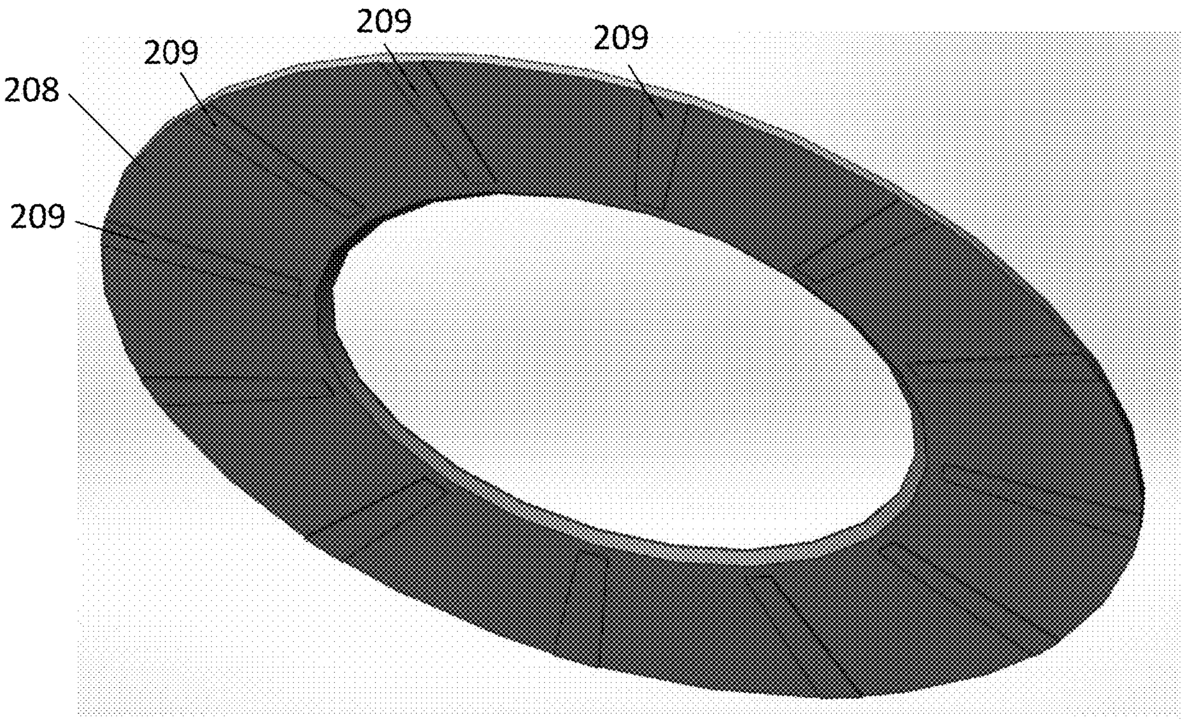
Figure 2H:
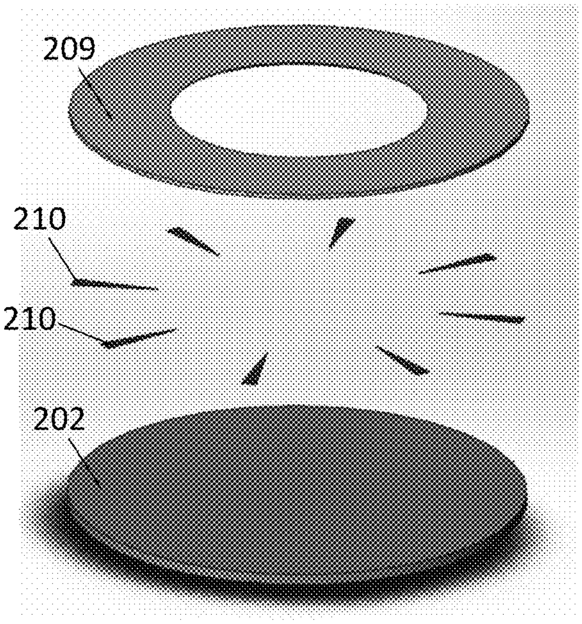
Figure 2I:
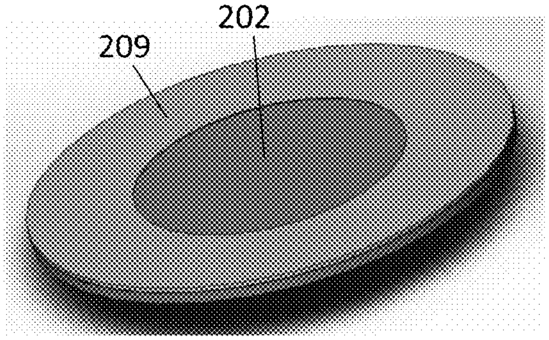
Figure 2J:
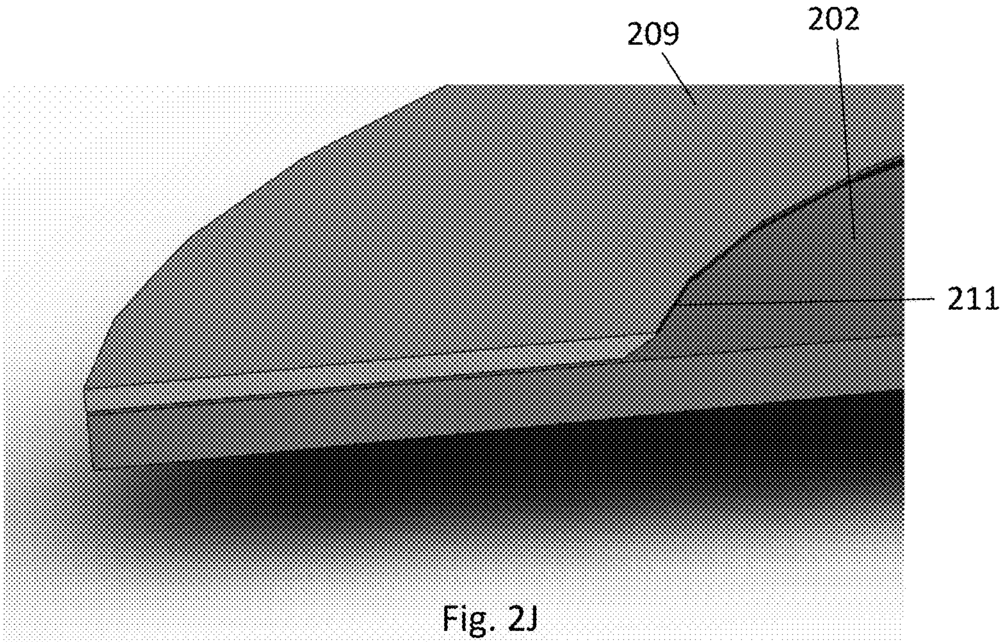

In embodiments, for example as shown in FIGS. 2E-2J, the substrate 202 may be part of a substrate assembly further including a cover slip 208. As shown in FIG. 2E, in embodiments, the substrate 202 may be circular and the cover slip 208 may be ring shape, i.e. circular with a circular central opening. The cover slip 208 may be coupled to the substrate 202 so that the cover slip 208 covers imaging portions 205 of the substrate while the opening of the cover slip 208 is over non-imaging portions of the substrate. The assembly may further include spacers so that a bottom surface of the cover slip is separated from the top surface of the substrate. In embodiments, for example as shown in 2G, the spacers 209 may be integrally formed with the cover slip 208, for example with molding. As shown, the spacers 209 may extend radially from the central opening of the cover slip to the circumference of the assembly. As shown in FIG. 2H the spacers 209 may be coupled to the substrate 202 with adhesive, for example tape 210. The spacers define flow channels between the cover slip and the substrate, and the assembly may be referred to as a flow cell in that fluid may flow over the surface of the substrate from the opening of the cover slip to an outer circumference of the assembly. The opening of the cover slip may include a bevel 211 to facilitate fluid entry into the flow channels.

Figure 3A:
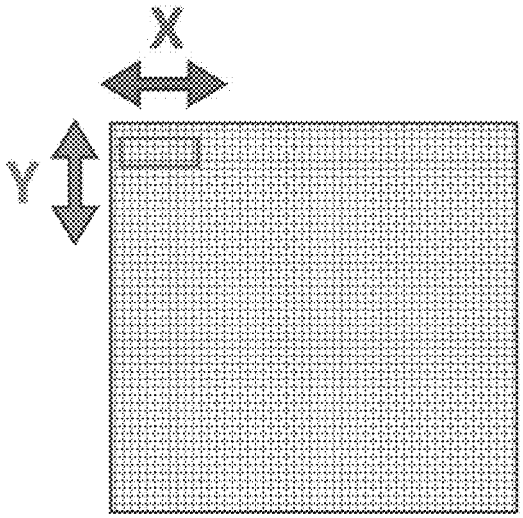
FIGS. 3A-3F show relative movements of an objective relative to a disk.
Figure 3B:
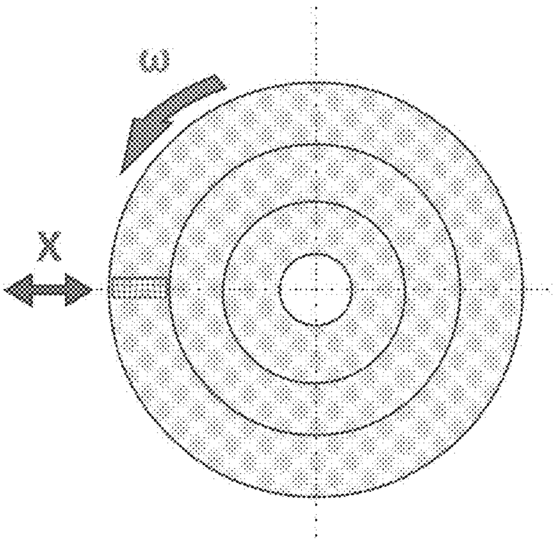
Figure 3C:
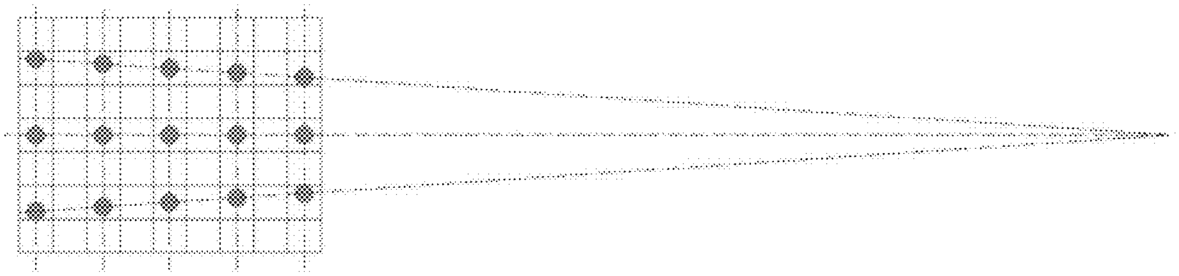

As noted above, in existing imaging systems, a rectangular substrate is translated relative to an objective in two orthogonal directions, for example in the X-direction and Y-direction as shown in FIG. 3A. In the present technology, a substrate is moved relative to the objective around a rotational axis, and may further be translated in a direction orthogonal to the rotational axis in order to orient the objective over any portion of the 2-dimensional substrate in order to image the substrate, for example as shown in FIG. 3B. The relative movements between a disk 201 and objective may be performed by actuators of an actuation system controlled by a control system in order to continuously position the FOV of the objective 104 so that FOV is maintained in focus on the desired portion of the substrate. In embodiments, due to the larger linear speed of portions of the substrate further from the rotational axis, nucleic acid template molecules (e.g., DNBs) may immobilized at more widely spaced positions toward the outer circumference of the substrate, for example as shown in FIG. 3C.

Figure 3D:
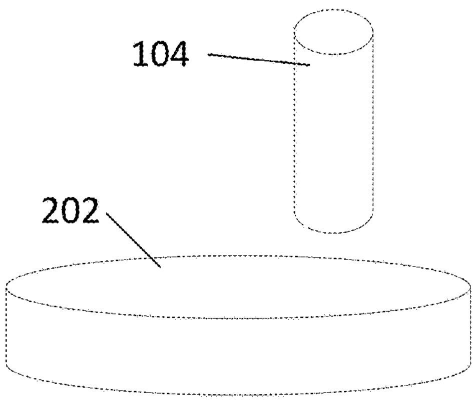
Figure 3E:
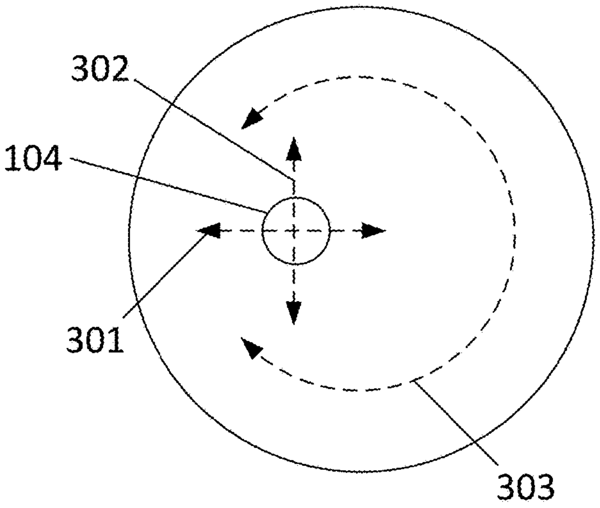
Figure 3F:
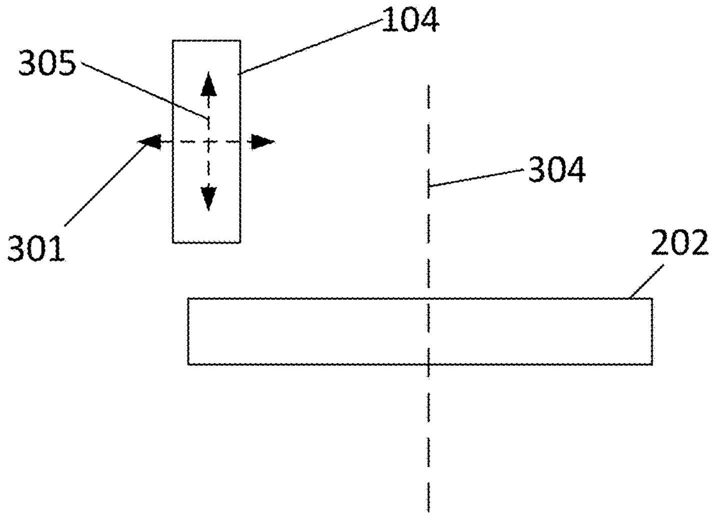

FIGS. 3D-3F shows views of a substrate 202 and the objective 104 in order to illustrate relative motion according to embodiments of the technology. As shown in FIG. 3D, the objective 104 is positioned over the substrate 202. As shown in FIG. 3E, the objective 104 may translate 301 relative to the disk in the X-direction, for example caused by the linear actuator 403 in which the disk and substrate are translated relative to the stationary objective. In some embodiments, the objective may optional also translate 302 relative to the disk in the Y-direction. Relative translation of the objective to the disk may occur during rotation 303 of the disk around the rotational axis 304. Relative motion of X-direction translation 301 and Z-axis rotation 303 may be used to image any portion of the substrate with the objective.

FIG. 3F shows a side view of the substrate 202 and the objective 204. As shown, and noted above regarding FIG. 3E, the objective may translate 301 relative to the substrate in the X-direction, for example caused by the linear actuator 403. Further, in embodiments, the objective may further translate 305 relative to the disk in the Z-direction, for example to maintain the substrate in the depth of focus of the objective.

In embodiments, actuators for performing these translational movements, shown in FIGS. 3D-3F, may be coupled to one or more of the disk assembly 200, the track assembly 400, and the detection system 102 associated with the objective 104.

A combination of the relative movements between the disk 201 and the objective 104 shown in FIGS. 3D-3F may be performed by actuators of an actuation system 901 controlled by a control system 900 in order to scan the objective 104 across a plurality of locations over the substrate 202 on the disk 201 in order to image the sequencing events.

In some embodiments, additional relative movement, for example X, Y, and/or Z rotational movements of the entire disk assembly 200 relative to the objective 104 may be performed by actuators of the actuation system 901 controlled by a control system 900 in order to precisely position, align and/or focus the objective 104 during imaging. The control system 900 may receive from any combination of input from one or more of position/acceleration/movement sensors of one or more components of the system, for example an encoder of actuator 203, and/or processed image data of the substrate 202 from the detection system 102, in order to control the relative movement of the objective 104 and disk 201.

Figure 4A:
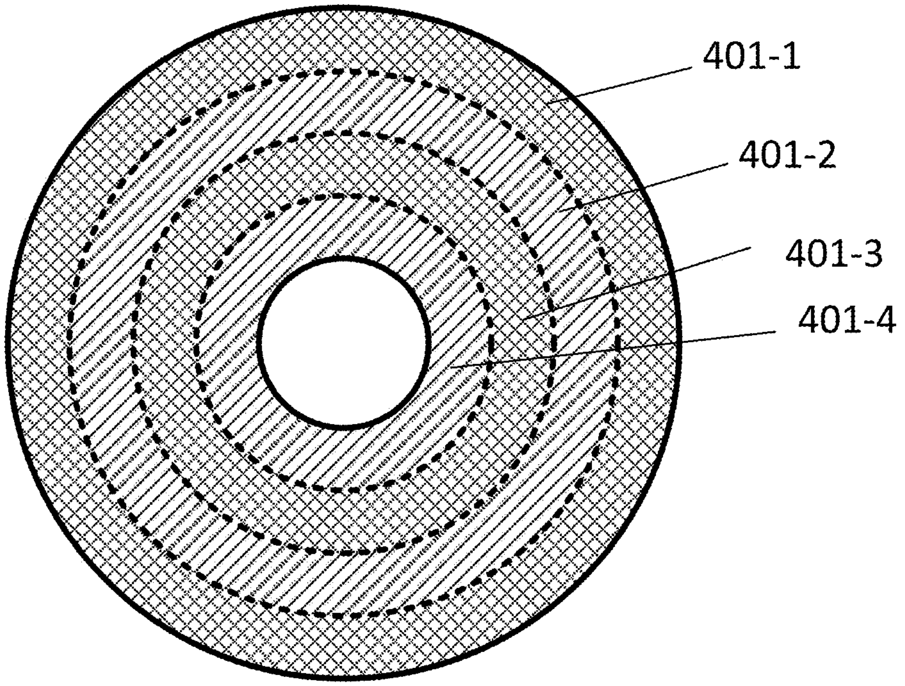
FIGS. 4A and 4B show substrates with ring and spiral imaging paths.
Figure 4B:
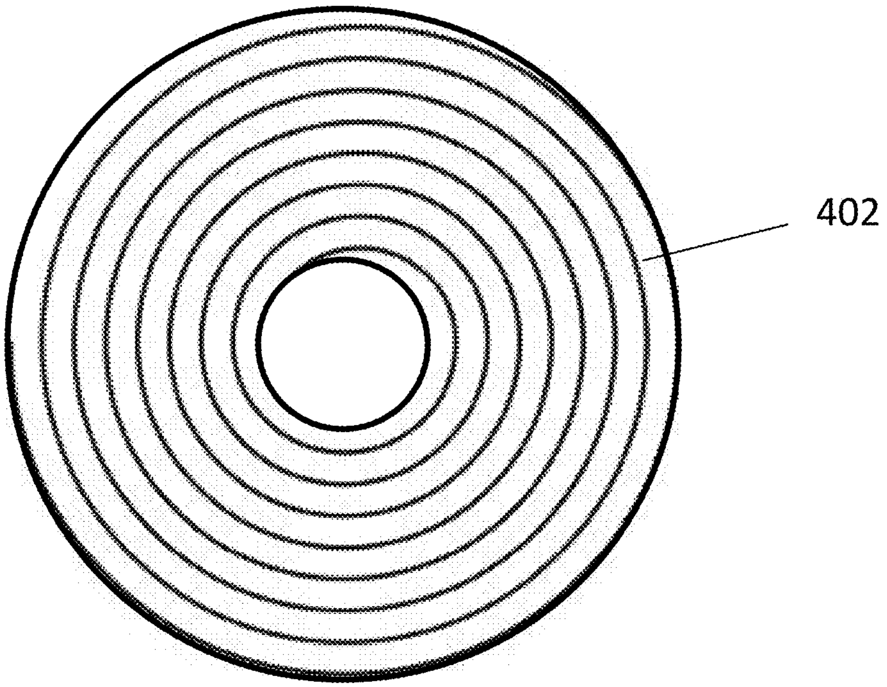

In embodiments, the imaging portions of a substrate 202 on the disk 201, for example as shown in FIGS. 4A and 4B, may be virtually and/or physically divided into an array of subregions during an imaging process. The substrate may define a patterned array of derivitized areas ("spots" or discrete spaced apart regions). The positions, or spots, may be organized as a regular, ordered array and are adapted to contain nucleic acid template molecules. In some embodiments, the array includes more than $10^5$, more than $10^6$, more than $10^7$ sites, more than $10^8$ sites, more than $10^9$ sites, or more than $10^{10}$ sites, such as from $10^5$ to $10^{11}$ sites or $10^6$ to $10^{10}$ sites. For example, the positions may be regions of the substrate surface derivatized to bind nucleic acid molecules (e.g., DNA nanoballs (DNBs), a template cluster produced by bridge amplification, or other templates), wells, or other structures. In some embodiments the surface of the substrate between spots is adapted to not bind nucleic acid molecules.

The control system may define one or more imaging paths on the substrate 202 within a control scheme for imaging the array of derivitized areas. The actuators of the actuation system are used to control the relative motion of the objective and substrates in order to image the substrates along the imaging paths. As shown for example in FIG. 4A, a substrate 202 may include a plurality of virtually defined imaging paths 401-1, 401-2, 401-3, 401-4, indicated in the figures as the patterned areas of the substrate between the dotted lines representing virtual boundaries between adjacent imaging paths.

The controller may cause the actuation system and detection system to sequentially scan the substrate along a plurality of ring imaging paths. To scan the plurality of ring imaging paths, the disk 201 may be rotated, for example at a constant speed, around the rotational axis, Z-axis, with the actuator 203. In embodiments, a constant rotation speed may result in a surface velocity for imaging of the substrate between 20 mm/sec to 100 mm/sec. The rotation speed may be a function of the size of FOV and the radial location of the scan. With the actuation system, the disk assembly 200 and the objective 104 may be moved relative to each other in the X-direction in order to cause the field of view of the objective 104 to be positioned over a first ring imaging path. The width of each imaging path may correspond to the width of the FOV of the objective. In embodiments, the substrate may define a radial width equal to the width of the FOV of the objective so that the entire substrate may be images in a single revolution of the disk.

In embodiments, the end of the objective 104 may be fixedly positioned within a predetermined distance so that the substrate is within depth of focus of the objective, and therefore does not necessitate actuation to focus. In some embodiments, the end of the objective 104 may be continually movably positioned by the actuation system within 20 microns of the substrate, within a precision of +/−0.05 microns in order for the substrate to be in focus. The detection system images the substrate 202 as the disk 201 makes a complete rotation in order to image an entire first ring imaging path. In embodiments including multiple concentric imaging rings, after imaging a first ring, the disk assembly 200 and the objective 104 may then be moved by the actuation system in order to cause the field of view of the objective 104 to be positioned over a second ring imaging path and imaging of the second ring is performed over the course of an entire rotation of the disk 201, which may be rotating at the constant speed while imaging the first ring imaging path and the second ring imaging path, and while the FOV is moved between the first ring imaging path and the second ring imaging path. In examples, an objective may have a field of view 1.5 mm wide, and after each rotation of disk may be translated in the X-direction by 1.5 mm, the width of the FOV, or less. For example, the translation distance may be less than the width of the FOV so that adjacent imaging paths overlap to ensure complete imaging of the entire substrate. The above steps for imaging an imaging path may be repeated for each imaging path on the substrate.

In embodiments, the control system may define imaging paths as spiral imaging paths, for example as shown in FIG. 4B. As shown, the spiral imaging path 402 may wind around a circumference of the substrate a plurality of times. The control system may cause the actuation system and detection system to scan the substrate along the one or more spiral imaging paths on the substrate 202. To scan a spiral imaging path 402, the disk 201 may be rotated at a constant speed around the rotational axis, Z-axis, with the actuator 203. With the actuators of the actuation system, the disk assembly 200 and the objective 104 are moved relative to each other in order to cause the field of view of the objective 104 to be positioned at the inner circumference or outer circumference of the spiral imaging path. Simultaneously with the disk rotating around the Z-axis, the actuation system causes the disk assembly 200 to translate in the X-direction, for example at a constant rate with the linear actuator. The rate of rotation and translation may be coordinated so that the disk assembly 200 translates in the X-direction the width of the field of view of the objective 104, or less as discussed above in order to have overlap during each rotation on the disk 201. In this way, an entire spiral imaging path, which may cover substantially all of a substrate, may be imaged in a single continuous imaging step wherein the rotation and translation are maintained at constant rates throughout the imaging of the spiral imaging path.

Utilizing the ring or spiral imaging paths with a continuously rotating disk 201 allows for increased imaging speed, and therefore an increased rate of generating sequencing data, compared to imagers which image a rectangular substrate by frequently stopping, slowing down, or changing the direction of the objective relative to the rectangular substrate between each transit of the objective relative to the substrate.

Figure 5A:
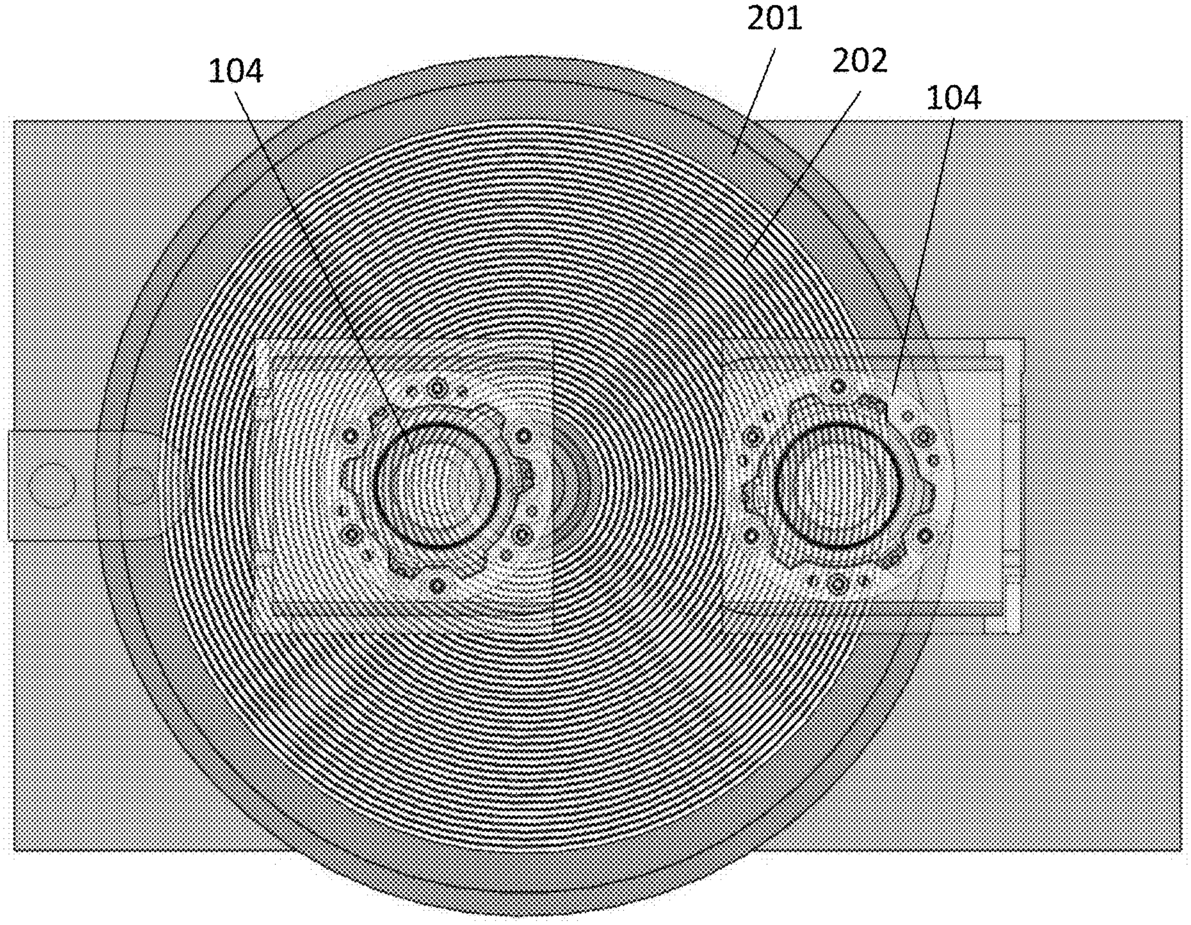
FIGS. 5A-5B show embodiments of an optical imaging system with multiple objectives.
Figure 5B:
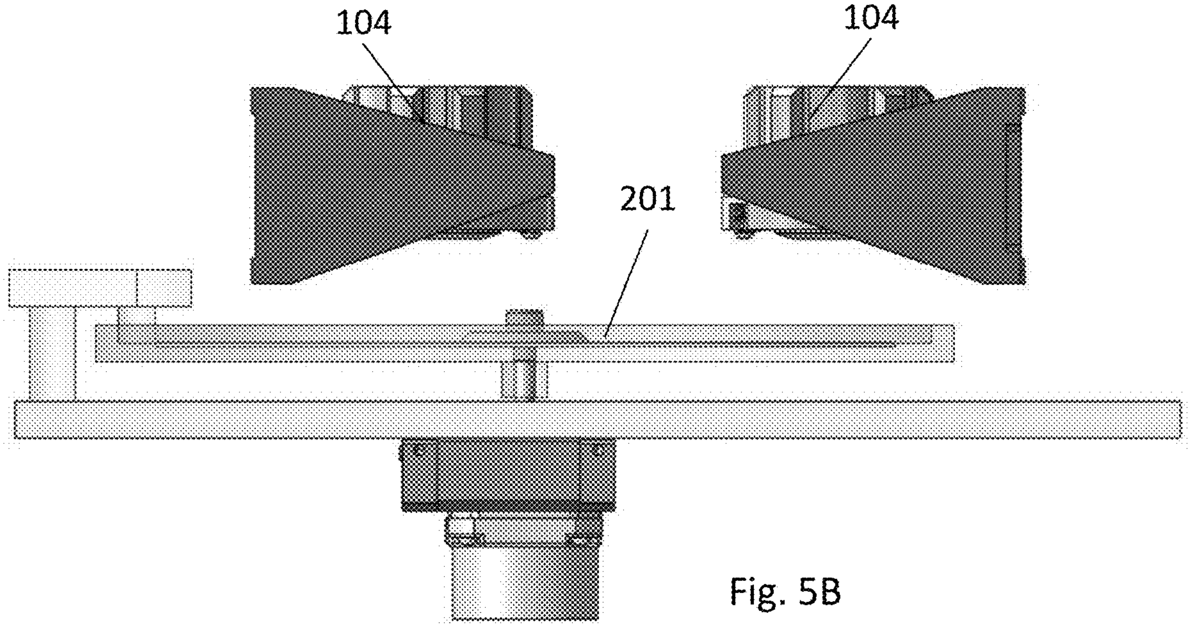
Figure 6:
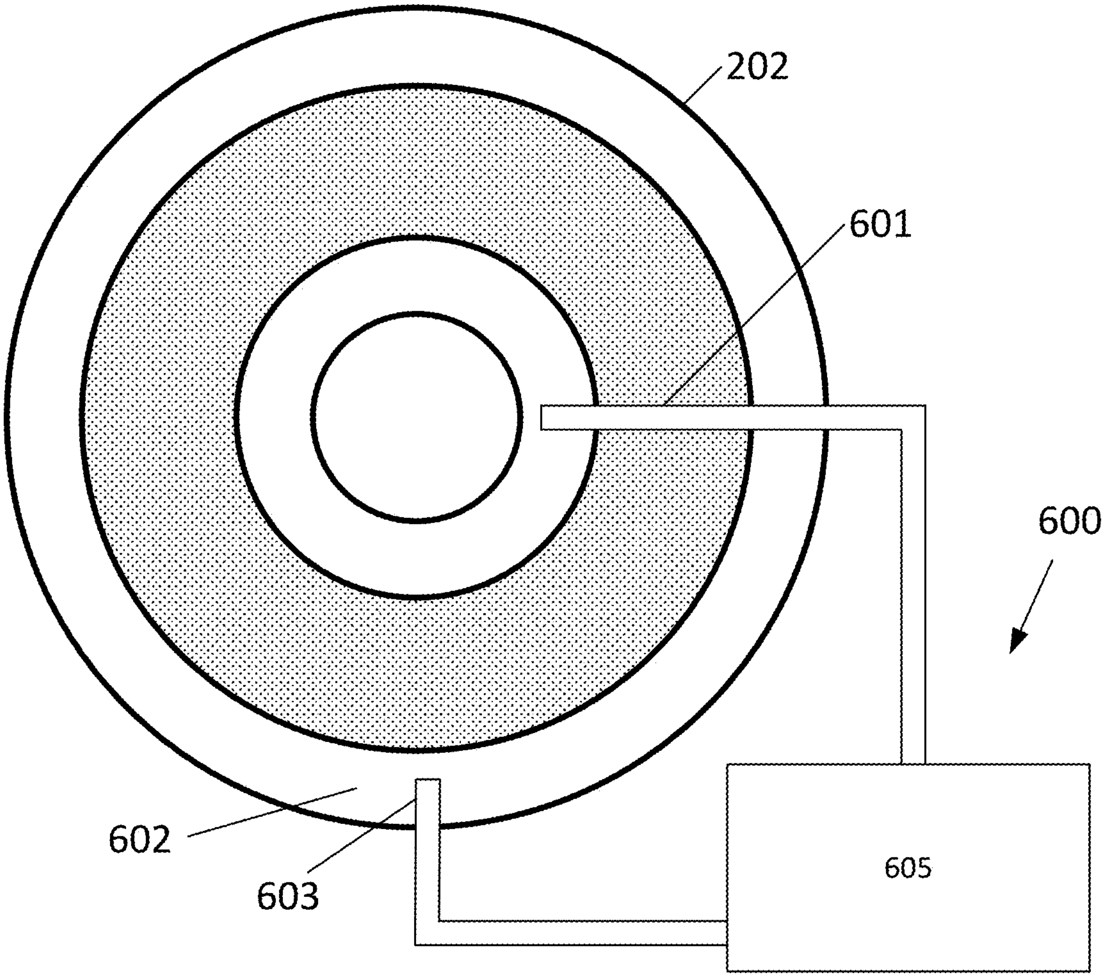
FIG. 6 shows a reagent delivery system.

The imaging speed of an imager with a rotating disk may further be increased compared to rectangular substrate imaging systems by including two or more objectives, for example as shown in FIGS. 5A and 5B. As shown, two objectives 104 may be positioned at different X-direction positions around the disk assembly 200. The objectives may be spaced so that the FOV of first objective on a first side of the rotational axis and at a starting position is at an outer circumference of the substrate and the FOV of the second objective on a second side of the rotational axis and at the starting position is at an inner circumference of the substrate so that translation in the X-direction causes relative movement of both FOVs toward a central circumference of the substrate. With these configurations, in embodiments, the entire substrate may be imaged with translation in the X-direction equally to half the radial width of the substrate, thus doubling the imaging speed by imaging two imaging paths simultaneously. In two objective embodiments, the adjacent imaging paths may be ring or spiral imaging paths. The actuation system may include actuators to separately cause relative movement for each of the two or more objectives relative to the disk assembly in order to separately position, align, and focus the different objectives.

As noted above, the one or more substrates on the disk may include nucleic acid template molecules (e.g., DNBs) immobilized at positions on the substrate. Prior to, during, and/or after imaging, reagents and wash buffers may be separately flowed over the substrate. For example, a fluid delivery system 600 may comprise a delivery element 601 for delivering reagents or other fluids on the substrate 202. The delivery element may be actuatable to be positioned over the disk at a position between the imaging portion of the substrate including the nucleic acid template molecules and the rotational axis, so that fluids may be delivered onto the rotating disk and/or substrate and centrifugal force causes the delivered fluid to spread evenly over the substrate. As noted above, the substrate may be part of a substrate assembly including flow guides which define flow paths to evenly distribute the fluid over the substrate via centrifugal force. In embodiments, the disk, and substrate, may be rotated at a higher speed when fluid is delivered than when the substrate is imaged. For example, during fluid delivery, the substrate may be rotated at 100 to 10,000+ RPMs.

During imaging, and during chemistry steps that occur prior to and subsequent to the imaging step, the surface of the substrate may generally be an aqueous environment, which may be necessary to preserve the nucleic acid templates disposed therein on the substrate. The environment adjacent to the disk may be controlled by an environment control system to have increased humidity in order to reduce and control evaporation of liquid on the substrate.

The reagents and wash buffers flowed over the substrate may flow past an outer circumference of the substrate into a drain portion 602 of the disk, wherein the fluid may be removed by a disposal or recycling system 605. A recycling system 605 may separately store fluids drawings to be reused in subsequent processes. For example, the previously used reagents may be stored and used in subsequent processes in order to provide the benefit reducing the total amount of reagents used.

The fluid delivery system may include a temperature control system as part of the environment control system, which may include heaters, coolers, and/or temperature sensors, in order to deliver fluids at a target temperature in order to promote sequencing reactions caused by the reagents.

Figure 7:
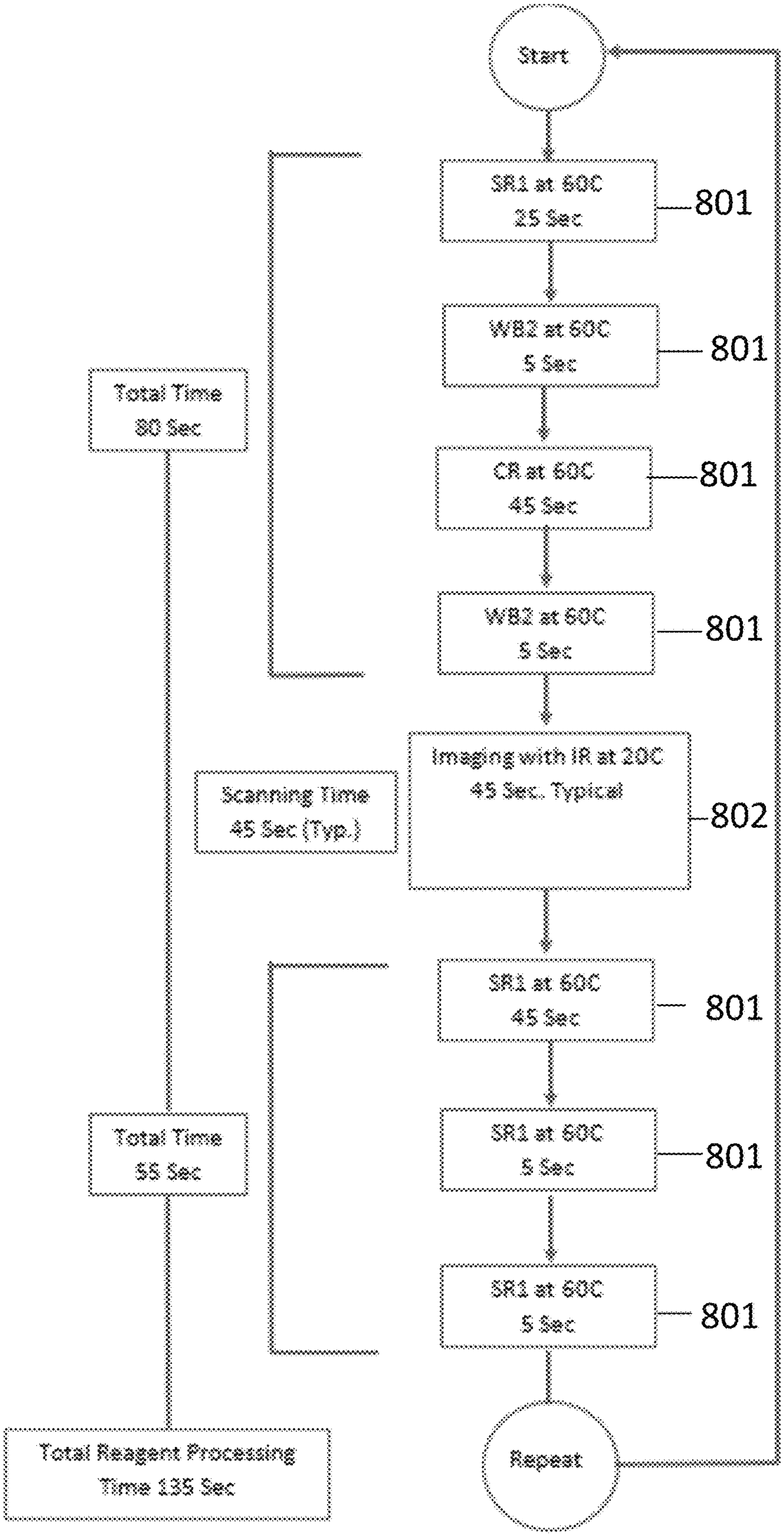
FIG. 7 shows an embodiment of a process diagram.

As shown in FIG. 7, an example sequencing process may include 7 reagent/wash buffer steps 801, and one imaging step 802. The steps may all be performed while the disk is rotating around the rotational axis. As noted above, the disk may be rotated at a higher velocity during reagent/wash buffer steps 801 than the imaging step 802 in order to spread the fluid over the substrate during reagent/wash buffer steps 801 and correspond to the camera speed in the imaging step 802.

Figure 9A:
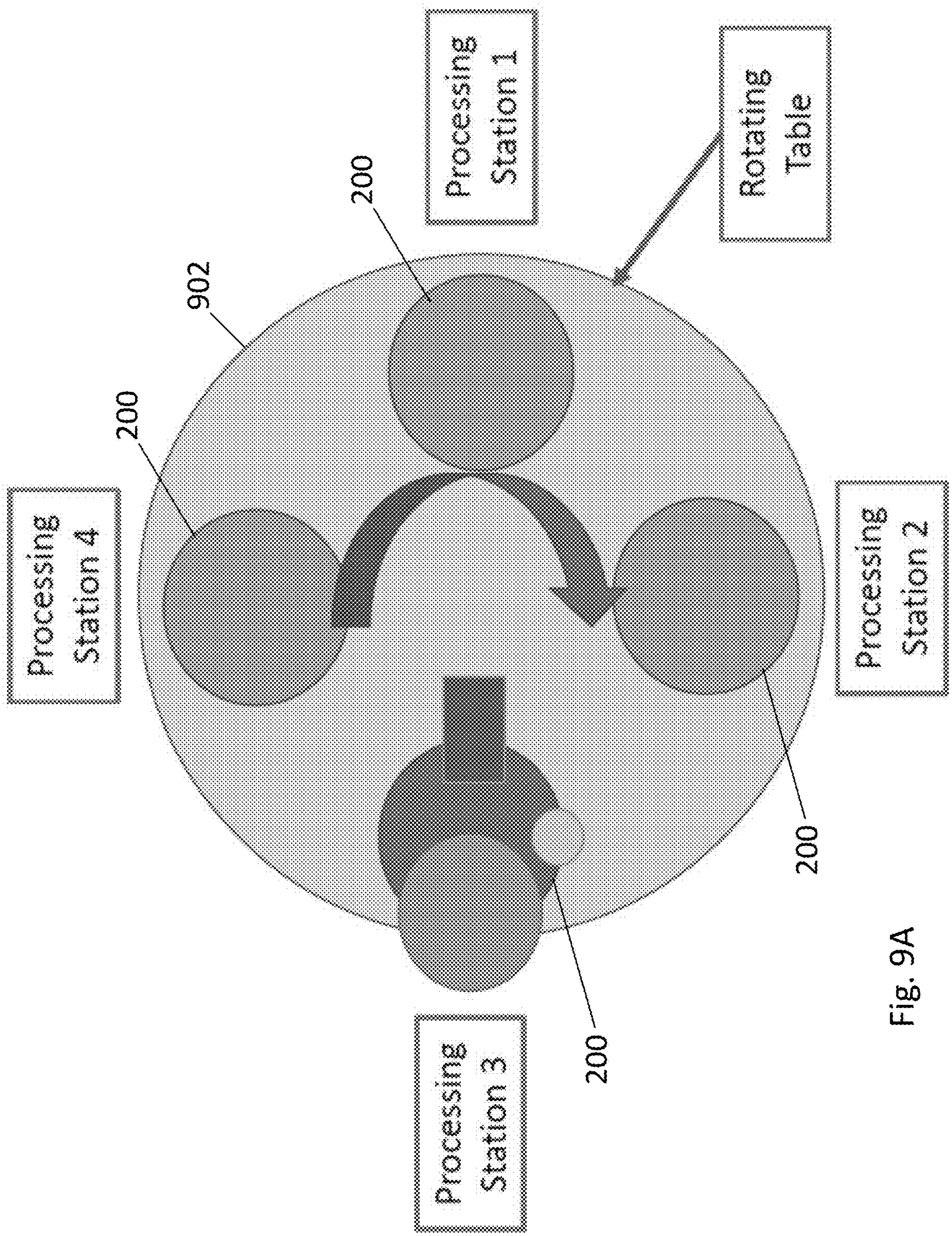
FIGS. 9A and 9B show an optical imaging system with multiple processing stations.
Figure 9B:
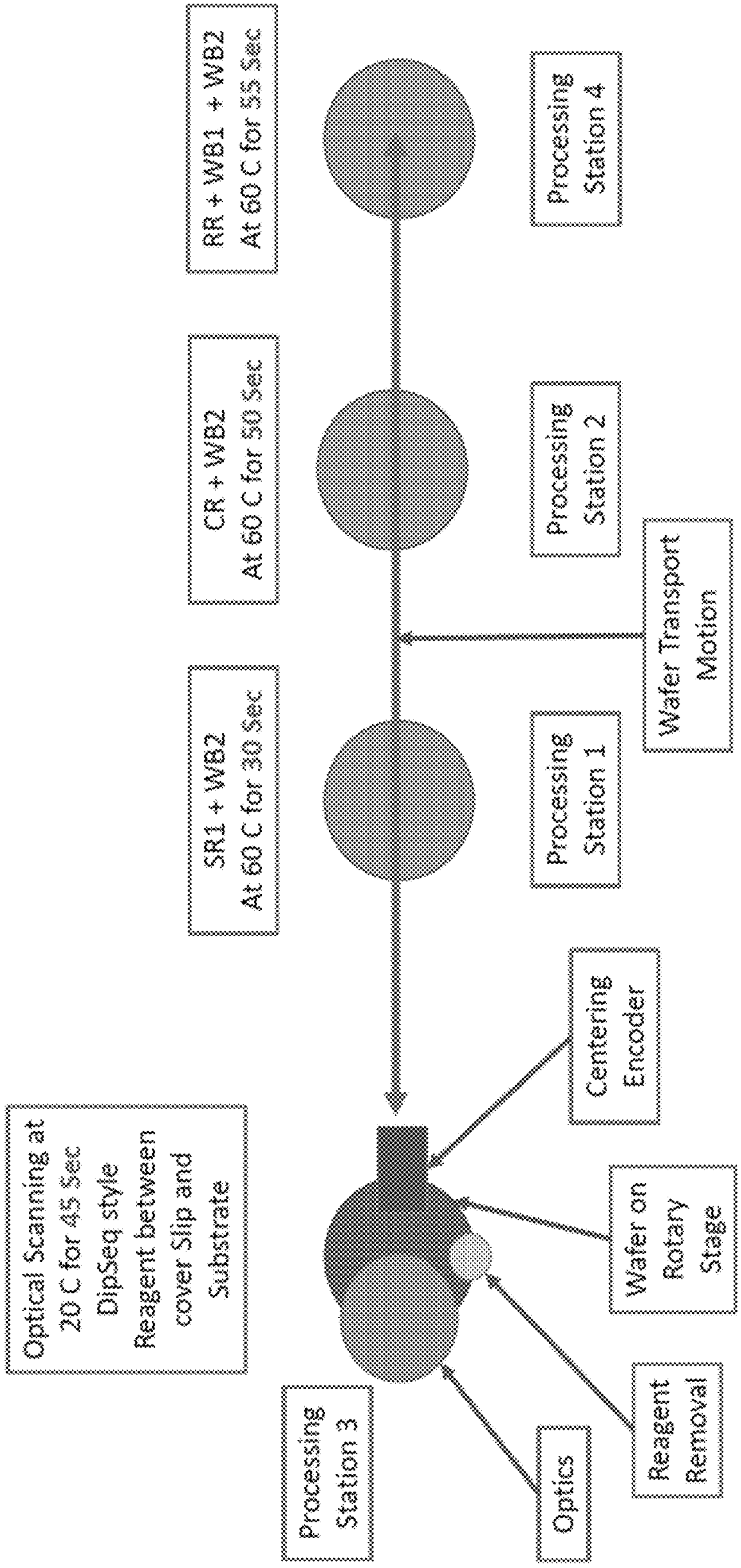

In embodiments, for example as shown in FIG. 9A, a plurality of disk assemblies may be coupled to a rotating stage 902. At any time, each of the plurality of disk assemblies 200 on the rotating stage 902 may be used to perform a different step in the sequencing process. In embodiments, two or more steps of a sequencing process may occur a processing station while one or more steps of the sequencing process are occurring simultaneously in another processing station, as shown in FIG. 9B. In embodiments, the number of processing stations may be the same or less than the total number of chemistry and imaging steps of the sequencing process. Once each processing station has performed the respective process step(s), each disk assembly may then be rotated shifted to the respective subsequent processing station for subsequent process step(s). For example, once an imaging step is performed at a first processing station, the rotating stage may move the disk assembly so that the objective may perform the imaging step on a second disk assembly. In other words, the sequencing process flow, for example as shown in FIG. 7, may be performed in parallel simultaneously for each disk assembly on the rotating stage, wherein each disk assembly on the rotating stage is on a different step of the sequencing process flow. This arrangement of processing stations may be advantageous including for reasons described in U.S. Pat. No. 10,351,909 B2 ("DNA sequencing from high density DNA arrays using asynchronous reactions"), which is incorporated by reference herein in its entirety.

Figure 8:
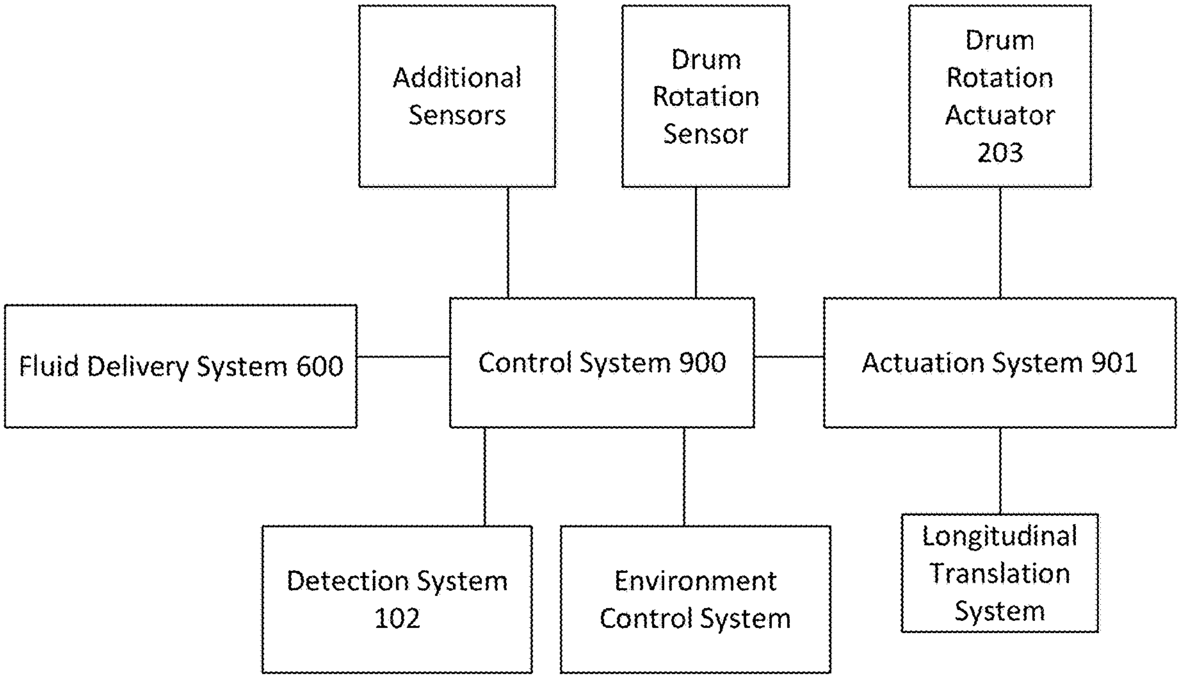
FIG. 8 shows a control system schematic.

FIG. 8 shows a schematic of the sub-systems of a sequencing system. As shown, a control system may be coupled to send and receive signals to each of the components of the system in order to control the system, as described above.

Figure 10:
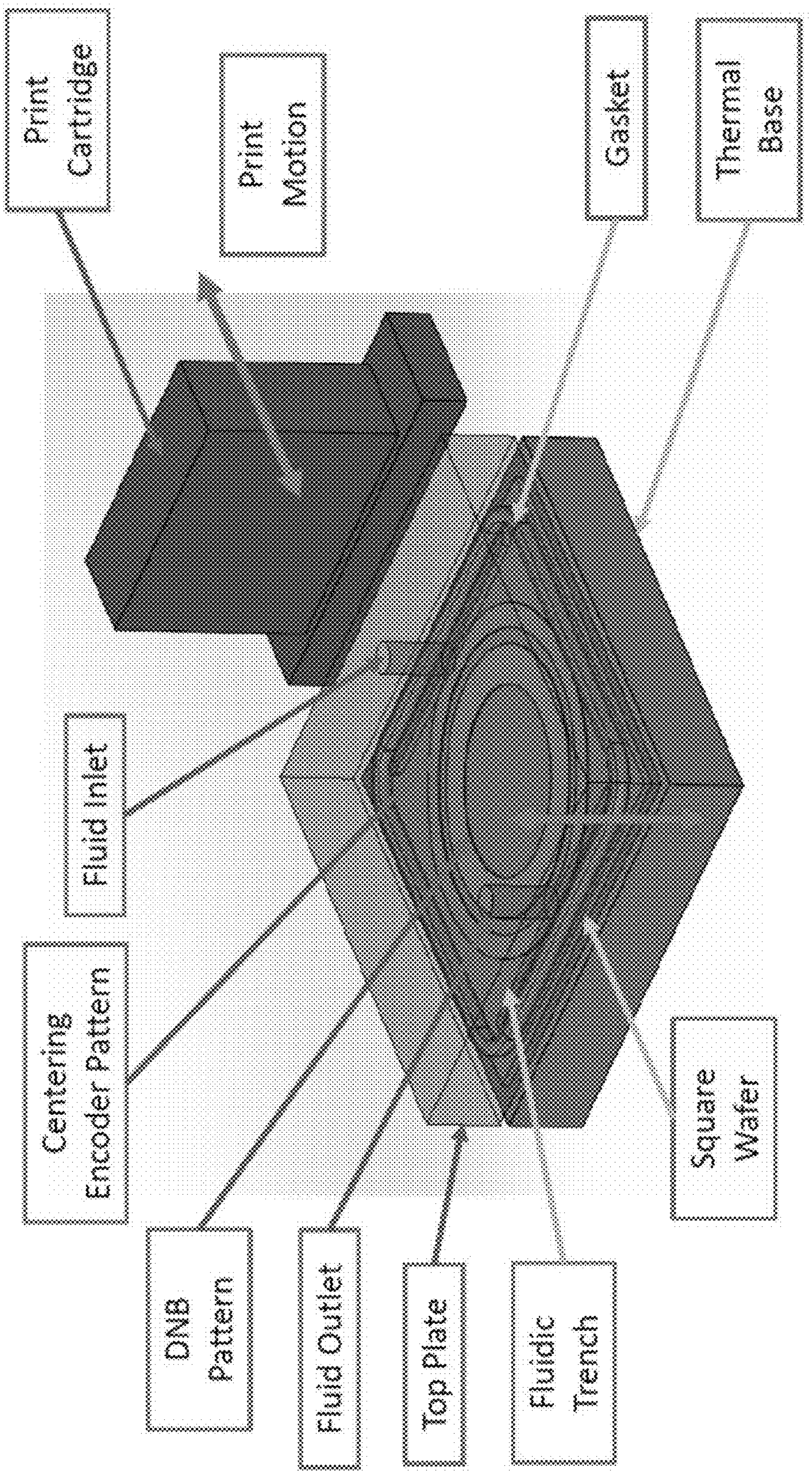
FIG. 10 shows a sequencing material deposition station.

In embodiments, a substrate may be prepared in a sequencing material deposition station, for example as shown in FIG. 10. The sequencing material deposition station may include a print cartridge to deposit genetic material on the substrate. In embodiments the substrate may include an encoder pattern in order for the control system to determine the position of the rotating substrate during imaging with an optical sensor. The encoder pattern may be used by the sequencing material deposition station to determine locations to deposit the genetic material.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

While the foregoing disclosure shows illustrative aspects of the disclosure, it should be noted that various changes and modifications could be made herein without departing from the scope of the disclosure as defined by the appended claims. The functions, steps and/or actions of the method claims in accordance with the aspects of the disclosure described herein need not be performed in any particular order. Furthermore, although elements of the disclosure may be described or claimed in the singular, the plural is contemplated unless limitation to the singular is explicitly stated.

What is claimed is:

1. A nucleic acid sequencing system, the system comprising:

- a rotatable disk defining a rotational axis perpendicular to a top surface;
- a substrate coupled to the disk and configured to support a plurality of nucleic acid samples;
- a cover coupled to the substrate and defining a flow path for fluid between the substrate and the cover;
- an actuation system configured to rotate the disk and the coupled substrate around the rotational axis; and
- a detection system configured to detect sequencing events on the substrate while the substrate is rotated relative to the detection system around the rotational axis by the actuation system.

2. The nucleic acid sequencing system of claim 1, wherein the cover comprises a central opening.

3. The nucleic acid sequencing system of claim 2, wherein the substrate comprises an imaging portion and a non-imaging portion, wherein the cover covers the imaging portion and the central opening is aligned with at least part of the non-imaging portion.

4. The nucleic acid sequencing system of claim 3, wherein the actuation system is further configured to translate the disk and substrate along a translation axis perpendicular to the rotational axis, and

- wherein the detection system is further configured to detect sequencing events on the substrate while the substrate is translated relative to the detection system along the translational axis by the actuation system.

5. The nucleic acid sequencing system of claim 4, wherein the detection system is an optical detection system comprising at least one objective.

6. The nucleic acid sequencing system of claim 5, wherein the at least one objective comprises two objectives configured to image portions of the substrate on opposite sides of the rotational axis.

7. The nucleic acid sequencing system of claim 6, wherein the cover comprises a cover slip, the system further comprising: a plurality of flow channels between the cover slip and the substrate.

8. The nucleic acid sequencing system of claim 7, further comprising:

- a carriage, wherein the disk is rotatably coupled to the carriage;
- a track assembly coupled to the carriage, wherein the actuation system is configured to translate the carriage in a direction perpendicular to the rotational axis in order for the at least one objective to image different portions of the substrate in a direction radial to the rotational axis as the substrate is rotating around the rotational axis.

9. The nucleic acid sequencing system of claim 1, wherein the cover is spaced apart from the substrate by a plurality of spacers.

10. The nucleic acid sequencing system of claim 9, wherein the spacers are radially oriented towards an outer circumference of the substrate.

11. The nucleic acid sequencing system of claim 10 wherein the flow path defined by the cover and the substrate comprises a plurality of flow channels extending towards the outer circumference of the substrate, the plurality of flow channels located between the substrate and the cover and at least partially separated by the spacers.

12. The nucleic acid sequencing system of claim 1, further comprising:

a fluid delivery system configured to deliver fluid onto the substrate in order to perform a sequencing process on the substrate.

13. The nucleic acid sequencing system of claim 1, wherein the cover comprises a cover slip, the system further comprising: a fluid delivery system configured to deliver fluid onto the substrate so that rotating the substrate causes the delivered fluid to flow between the cover slip and substrate due to centrifugal force.

14. The nucleic acid sequencing system of claim 13, wherein the fluid delivery system is configured to deliver fluid proximate to the rotational axis so that rotation of the substrate causes the dispensed fluid to flow toward a perimeter of the substrate and cover the entire substrate.

15. The nucleic acid sequencing system of claim 14, wherein the fluid delivery system is configured to deliver fluid onto the substrate through a central opening of the cover slip.

16. The nucleic acid sequencing system of claim 15, wherein the disk comprises a fluid retrieval portion configured to drain fluid delivered by the fluid delivery system.

17. The nucleic acid sequencing system of claim 16, wherein the fluid delivery system comprises a recycling system for capturing fluid drained from the retrieval portion in order to reuse the fluid.

18. The nucleic acid sequencing system of claim 17, wherein the substrate comprises an ordered array of discrete spaced apart regions, wherein the discrete spaced apart regions are configured to immobilize nucleic acids.

19. The nucleic acid sequencing system of claim 18, further comprising:

nucleic acids immobilized on the discrete spaced apart regions of the array, wherein the nucleic acids immobilized on the discrete spaced apart regions are DNA nanoballs (DNBs) or PCR products.

20. The nucleic acid sequencing system of claim 19, wherein a spacing of the discrete spaced apart regions is greater at outer portions of the substrate than at inner portions of the substrate.

* * * * *